(12) United States Patent
Yamauchi et al.

(10) Patent No.: US 7,466,419 B2
(45) Date of Patent: Dec. 16, 2008

(54) SPECTRAL INSTRUMENT

(75) Inventors: Kazunori Yamauchi, Hamamatsu (JP); Hiroyuki Sugiyama, Hamamatsu (JP)

(73) Assignee: Hamamatsu Photonics K.K., Hamamatsu-shi, Shizuoka (JP)

( * ) Notice: Subject to any disclaimer, the term of this patent is extended or adjusted under 35 U.S.C. 154(b) by 128 days.

(21) Appl. No.: 10/547,128

(22) PCT Filed: Feb. 26, 2004

(86) PCT No.: PCT/JP2004/002246
§ 371 (c)(1),
(2), (4) Date: Feb. 15, 2007

(87) PCT Pub. No.: WO2004/076997
PCT Pub. Date: Sep. 10, 2004

(65) Prior Publication Data
US 2007/0229831 A1    Oct. 4, 2007

(30) Foreign Application Priority Data
Feb. 28, 2003    (JP)    ............... 2003-054701

(51) Int. Cl.
*G01J 3/51*    (2006.01)
(52) U.S. Cl. ...................... 356/419; 356/417
(58) Field of Classification Search .................. 356/419
See application file for complete search history.

(56) References Cited
U.S. PATENT DOCUMENTS
3,679,291 A    7/1972    Apfel et al.

5,995,235 A    11/1999    Sui et al.
6,249,348 B1    6/2001    Jung et al.
6,362,888 B1    3/2002    Jung et al.

FOREIGN PATENT DOCUMENTS

| JP | 54-103055 | 8/1979 |
|---|---|---|
| JP | 57-184937 | 11/1982 |
| JP | 59-131124 | 7/1984 |
| JP | 59-170734 | 9/1984 |
| JP | 60-252303 | 12/1985 |
| JP | 61-198203 | 9/1986 |
| JP | 61-205906 | 9/1986 |
| JP | 62-57138 | 4/1987 |

(Continued)

OTHER PUBLICATIONS

Marko Jankovec et al., "Numerical and Experimental Study of a-Si:H based Ultraviolet Sensitive Detectors", Journal of Non-Crystalline Solids 299 302 (2002), pp. 1229-1233.

*Primary Examiner*—F. L Evans
(74) *Attorney, Agent, or Firm*—Drinker Biddle & Reath LLP

(57) ABSTRACT

In this spectral instrument, a plurality of interference filters 31, 32 . . . with transmitting wavebands different from each other are arranged in order so that light reflected by a specific interference filter 31 is made incident on the interference filter 32 on the next stage, and at positions on which light transmitted through each interference filter is made incident, photodetecting devices 41, 42 . . . are provided, wherein a silver thin film 31a with a thickness of 20 to 200 nm is provided on the light incidence surface side of the interference filter 31 on the first stage.

11 Claims, 11 Drawing Sheets

FOREIGN PATENT DOCUMENTS

| | | |
|---|---|---|
| JP | 1-300202 | 12/1989 |
| JP | 07-020313 | 1/1995 |
| JP | 10-062246 | 3/1998 |
| JP | 11-006766 | 1/1999 |
| JP | 2001-201655 | 7/2001 |
| JP | 2002-517012 | 6/2002 |
| WO | 03/016842 | 2/2003 |
| WO | 03/038483 | 5/2003 |

Fig.7

| REFLECTION TYPE SPECTROSCOPE CHANNEL | [CONVENTIONAL EXAMPLE] BAND-PASS FILTER ONLY | [EXAMPLE] ADD AN EVAPORATED FILM ON THE FRONT SURFACE OF THE BAND-PASS FILTER. | | | | |
|---|---|---|---|---|---|---|
| | | Ag(20nm) | Ag(40nm) | Ag(60nm) | Ag(80nm) | Ag(100nm) |
| Ch.1(340nm) | 16.0 | 10.2 | 6.5 | 4.8 | 2.4 | 1.3 |
| Ch.2(405nm) | 103.5 | 87.1 | 92.6 | 102.2 | 107.1 | 108.8 |
| Ch.3(450nm) | 221.4 | 189.9 | 224.8 | 234.3 | 246.0 | 248.0 |
| Ch.4(505nm) | 125.5 | 225.7 | 440.0 | 445.7 | 492.1 | 488.2 |
| Ch.5(546nm) | 94.2 | 209.1 | 460.4 | 464.0 | 521.9 | 502.3 |

Fig.9

| β-NADH CONCENTRATION | [CONVENTIONAL EXAMPLE] BAND-PASS FILTER ONLY | [EXAMPLE] ADD AN EVAPORATED FILM TO THE FRONT SURFACE OF THE BAND-PASS FILTER. | | | | |
|---|---|---|---|---|---|---|
| | | Ag(20nm) | Ag(40nm) | Ag(60nm) | Ag(80nm) | Ag(100nm) |
| 0 | 13210.0 | 7635.0 | 5293.0 | 4057.0 | 1932.0 | 1097.4 |
| 20 | 5218.0 | 1812.0 | 1125.0 | 831.3 | 420.0 | 235.9 |
| 60 | 2005.0 | 382.6 | 151.9 | 89.0 | 40.8 | 23.0 |
| 80 | 1890.0 | 266.6 | 73.2 | 34.9 | 12.7 | 6.7 |
| 100 | 1842.0 | 227.8 | 46.9 | 16.4 | 3.4 | 1.8 |

Fig.10

| β-NADH CONCENTRATION | [CONVENTIONAL EXAMPLE] BAND-PASS FILTER ONLY | [EXAMPLE] ADD AN EVAPORATED FILM TO THE FRONT SURFACE OF THE BAND-PASS FILTER. | | | | |
|---|---|---|---|---|---|---|
| | | Ag(20nm) | Ag(40nm) | Ag(60nm) | Ag(80nm) | Ag(100nm) |
| 0 | 0.000 | 0.000 | 0.000 | 0.000 | 0.000 | 0.000 |
| 20 | 0.403 | 0.625 | 0.673 | 0.688 | 0.663 | 0.668 |
| 60 | 0.819 | 1.300 | 1.542 | 1.659 | 1.675 | 1.679 |
| 80 | 0.844 | 1.457 | 1.859 | 2.065 | 2.182 | 2.218 |
| 100 | 0.856 | 1.525 | 2.053 | 2.395 | 2.753 | 2.780 |

SPECTRAL INSTRUMENT

TECHNICAL FIELD

The invention relates to a spectral instrument to be used for, for example, a blood test.

BACKGROUND ART

Spectral instruments are units for measuring absorbance/reflectance of a test sample by changing the intensity of light transmitted/reflected by the test sample, and are used in various fields. When a spectral instrument is applied to, for example, color measurement or blood tests, in the light transmitted through the test sample, absorbance is measured for a plurality of optic elements with different wavelengths, that is, for each wavelength of multi-wavelengths. As such an instrument, a rotor plate-type spectral instrument disclosed in Japanese Published Unexamined Patent Publication No. S59-131124 is available. This spectral instrument makes it possible to detect multi-wavelengths by mechanically rotating a rotor plate so that a filter that transmits an optic element of a wavelength to be detected is positioned in the light path.

However, the rotor plate-type spectral instrument selects a filter by mechanically rotating the rotor plate, so that it takes time to detect multi-wavelengths. Quick testing of many samples and many items is required in a blood test, however, the rotor plate-type instrument cannot meet this requirement.

As a unit to meet this requirement, for example, the half mirror-type spectral instruments disclosed in Japanese Published Unexamined Patent Publication No. H11-6766 and Japanese Published Unexamined Patent Publication No. S59-170734 are available. These spectral instruments are structured to detect multi-wavelengths by a plurality of half mirrors and a plurality of light receiving devices. The half mirror type spectral instrument divides incident light into transmitted light and reflected light by half mirrors, and uses the transmitted light as incident light on the half mirror positioned next, thereby detecting multi-wavelengths. Therefore, in comparison with the above-described rotor plate type spectral instrument that detects multi-wavelengths by mechanically selecting a wavelength, multi-wavelengths can be detected at high speed.

DISCLOSURE OF THE INVENTION

However, according to the half mirror type spectral instrument, a light flux is divided into ½ by one half mirror. Therefore, in a light receiving device positioned next, the incident light is extremely weakened, so that the S/N ratio is lowered, and the detection efficiency of the optic element detection sensitivity lowers. For example, when eight half mirrors are provided and 9 kinds of wavelengths are detected, the intensity of light transmitted through the eighth half mirror becomes $(½)^8=1/256$ of the intensity of light transmitted through the first one, so that the detection efficiency of the optic element of this wavelength becomes extremely low. In order to cope with this, the light amount from the light source must be increased, however, this results in an increase in power consumption.

The invention was made to solve this problem, and an object thereof is to provide a spectral instrument which can detect a plurality of optic elements with different wavelengths with high detection efficiency.

The spectral instrument relating to the invention includes a plurality of interference filters with different transmitting wavebands made of dielectric multilayer films arranged in order so as to make light reflected by a specific interference filter incident on the next-stage interference filter, wherein a silver thin film with a thickness of 20 to 200 nm is provided on the light incidence surface side of the first stage filter in this spectral instrument.

In this spectral instrument, since the transmitting wavebands of the interference filters are different from each other, light with different wavelengths are transmitted through the interference filters and detected by photodetecting devices, whereby spectroscopy is carried out. The reflected light intensity of the interference filter is attenuated toward the rear stage side. Therefore, in order to detect sufficient light by photodetecting devices on the rear side, in this spectral instrument, a silver thin film with a thickness of 20 nm or more is provided on the light incidence surface side of the interference filter on the first-stage from the light source to improve the reflection performance thereof, and the thickness of the silver thin film is set to 200 nm or less so as to prevent attenuation of the light intensity to be transmitted through this interference filter. Thereby, a plurality of optic elements with different wavelengths can be detected with high detection efficiency.

The spectral instrument according to the invention is provided with a light transmitting protection member that sandwiches the silver thin film with the interference filter. The silver thin film is easily damaged, so that the silver thin film can be protected by providing the light transmitting protective film. Light with a target wavelength transmitted through the light transmitting protect member is transmitted through the silver thin film and the interference filter and reaches the photodetecting device.

Silver deteriorates its reflectance due to oxidation caused by air, so that in this spectral instrument, the light transmitting protection member is made of dampproof glass, and by depositing the silver thin film on the light transmitting protection member, the reflection interface formed by the silver thin film is damp-proofed, and after forming the silver thin film, the silver thin film is optically coupled with the interference filter. Thereby, deterioration prevention and protection of the silver thin film can be simultaneously realized, and due to optical coupling to the interference filter, a target wavelength is transmitted through the light transmitting protection member, the silver thin film, and the interference filter with high efficiency, and wavelengths other than the target wavelength are sufficiently reflected.

Concerning this optical coupling, the spectral instrument of the invention is further provided with a pressing member that presses the light transmitting protection member against the interference filter side so that the silver thin film comes into close contact with the interference filter, and according to the improvement in close contact, the optical coupling efficiency is improved.

In the spectral instrument relating to the invention, the silver thin film can be directly deposited on the interference filter. In this case, optical coupling between the interference filter and the silver thin film becomes easy.

BRIEF DESCRIPTION OF THE DRAWINGS

FIG. 7 is a table showing output values (nA) from photodiodes for each channel (Ch) in the spectral instrument;

FIG. 9 is a table showing output values (nA) of a photodetector on the first stage when β-NADH (substance that absorbs a transmitting wavelength (340 nm) of ch1) is put in a sample cell;

FIG. 10 is a table in which the output values of FIG. 9 are converted into absorbances.

BEST MODES FOR CARRYING OUT THE INVENTION

Hereinafter, spectral instruments according to embodiments are described with reference to the drawings. The same symbols are used for the same components and overlapping description is omitted.

Figure 1:
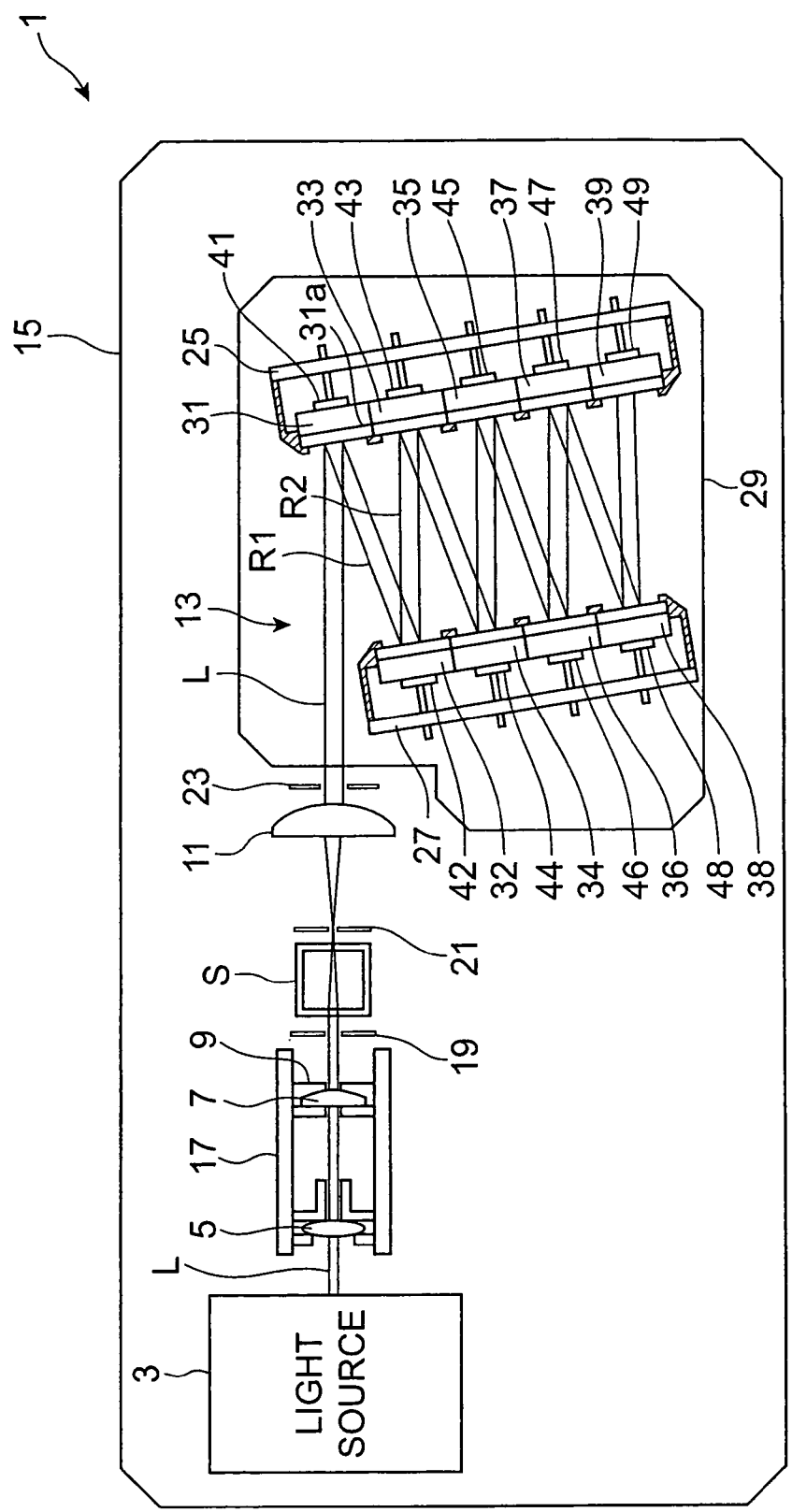
FIG. 1 is a schematic view of a spectral instrument according to a first embodiment.

FIG. 1 is a schematic view of a spectral instrument according to a first embodiment. The spectral instrument 1 detects optic elements with nine wavelengths, and includes a light source 3 including, for example, an iodine bulb of 20 W, two lenses 5 and 7 for condensing light L that has been emitted from the light source 3 while slightly expanding, an aperture 9 through which the light L transmitted through the lenses 5 and 7 pass, a lens 11 which converts the light L that has passed through the aperture 9 and transmitted through a sample cell S that contains a test sample (for example, blood) into a roughly collimated light beam, and a spectral part 13 on which the light L converted into a roughly collimated light beam by the lens 11 is made incident. These components forming the spectral instrument 1 are housed in a casing (cylinder) 15. The roughly collimated light beam is a light beam close to collimated light, and in actuality, the output light of the lens 11 is imaged on a specific position. The image forming position by this lens 11 can be set on the first-stage filter or between the filters. Namely, this image forming position is set at a position where finally necessary information is efficiently obtained.

The lens 5, the lens 7, and the aperture 9 are retained by a retaining part 17, and the lens 5, the lens 7, and the aperture 9 are arranged in order along the light path of the light L. The section size of the light L when the light L is made incident on the sample cell S is regulated by the lens 5, the lens 7, and the aperture 9. This section is positioned at a right angle with respect to the light L advancing direction, and has a size of, for example, 3 mm vertically and 3 mm horizontally.

In the light path between the aperture 9 and the lens 11, a place while the sample cell S is positioned is set. Slits 19 and 21 are disposed so as to sandwich this setting place. In the light path between the lens 11 and the spectral part 13, a slit 23 is disposed.

The structure of the spectral part 13 is described in detail. The spectral part 13 includes nine interference filters 31 through 39, nine photodiodes 41 through 49 which correspond to the respective interference filters 31 through 39 and detect optic elements transmitted through the corresponding interference filters 31 through 39. The photodiodes 41 through 49 are an example of the photodetecting devices. As a photodiode to be used in this embodiment, for example, an Si photodiode is available.

The interference filters 31, 33, 35, 37, and 39 are arranged so that their incidence planes form a line in one direction, and in this state, these are retained by the retaining part 25. The retaining part 25 is disposed so that the light L made incident on the spectral part 13 is made incident on the interference filter 31 at a predetermined angle. To the light outgoing surfaces of the interference filters 31, 33, 35, 37, and 39, photodiodes 41, 43, 45, 47, and 49 are attached. Thereby, the photodiodes detect optic elements transmitted through the corresponding interference filters.

The interference filters 32, 34, 36, and 38 are also arranged so that their incidence planes form a line in one direction, and in this state, these are retained by a retaining part 27. The retaining part 27 is disposed at a position that does not disturb the light path until the light L made incident on the spectral part 13 is made incident on the interference filter 31 so that the interference filters retained by the retaining part 27 face the interference filters retained by the retaining part 25.

To the respective light outgoing surfaces of the interference filters 32, 34, 36, and 38, photodiodes 42, 44, 46, and 48 are attached. Thereby, the photodiodes detect optic elements transmitted through the corresponding interference filters. In the spectral part 13, an electronic circuit (not shown) of an amplifier, etc., that amplifies the optic elements detected by the respective photodiodes 41 through 49 is provided. These components forming the spectral part 13 are housed in a casing (cylinder) 29.

The interference filters 31 through 39 divide each incident light into optic elements to be reflected and an optic element to be transmitted. By arranging the retaining parts 25 and 27 as described above, the optic elements to be reflected become light to be made incident on the interference filter positioned next, whereby light L from the light source 3 is transmitted in the order corresponding to the interference filters 31 through 39. The interference filters (dielectric multilayers) 31 through 39 have functions as band filters, and optic elements of wavelengths (central wavelengths of the transmitting wavebands) to be transmitted by these are as follows.

The interference filter 31: 340 nm, the interference filter 32: 405 nm, the interference filter 33: 450 nm, the interference filter 34: 505 nm, the interference filter 35: 546 nm, the interference filter 36: 570 nm, the interference filter 37: 600 nm, the interference filter 38: 700 nm, and the interference filter 39: 800 nm.

Next, operations of the spectral instrument 1 are described with reference to FIG. 1. Light L emitted from the light source 3 passes through the slit 19 after its section size is regulated to a predetermined value by the lenses 5 and 7 and the aperture 9, and is then made incident on the sample cell S. After being transmitted through the sample cell S, the light L passes through the slit 21 and is made incident on the lens 11. The light L is condensed by the lens 11 and made incident on the spectral part 13 through the slit 23. The light L (in particular, after the lens 11) indicates effective light of its elements to be propagated to the next-stage device.

The sample cell S is disposed within the light path between the light source 3 and the first-stage interference filter 31, and information on the substance in the sample cell S is transmitted to the interference filter 31. In addition, a casing 15 for housing the light source 3, the sample cell S, the interference filter 31, and the photodetecting device 41 is provided, and the casing 15 keeps the internal temperature and environment constant.

Light L made incident on the spectral part 13 is made incident on the incidence plane of the interference filter 31, and divided into an optic element to be transmitted and optic elements R1 to be reflected by the interference filter 31. The optic element to be transmitted is mainly an optic element with a wavelength of 340 nm, and is detected by the photodiode 41.

The interference filter has characteristics to reflect optic elements other than the optic element with a wavelength to be transmitted. Therefore, the optic elements R1 to be reflected by the interference filter 31 contain high intensities of optic elements with wavelengths to be transmitted through the interference filters 32 through 39 positioned in the rear of the order. The optic elements R1 to be reflected are made incident on the incidence plane of the interference filter 32, and divided into an optic element to be transmitted and optic elements R2 to be reflected by the interference filter 32. The optic element to be transmitted by the interference filter 32 is mainly an optic element with a wavelength of 415 nm, and this optic element is detected by the photodiode 42. The reflected light R2 contains high intensities of optic elements with wavelengths to be transmitted through the interference filters 33 through 39 positioned in the rear of the order for the same reason as described above.

Optic elements transmitted through the interference filters 33 through 39 are successively detected by the photodiodes 43 through 49 in the same manner. Therefore, according to the spectral instrument 1, optic elements of nine wavelengths can be detected.

Light made incident on the spectral instrument 1 is made incident on a photodetector (31, 41) on the first stage at an angle of incidence θ, and light reflected by the photodetector (31, 41) is made incident on the photodetector (32, 42) on the next stage at an angle of incidence θ, and light reflected by the photodetector (32, 42) is made incident on the photodetector (33, 43) on the next stage at an angle of incidence θ. Namely, the angle of incidence θ of the light on the first interference filter 31 is greater than 0° and equal to or smaller than 10°, and the angle of incidence θ of the light on the second interference filter 32 is greater than 0° and equal to or smaller than 10°. In this example, θ=8°. When the angle of incidence θ exceeds 10°, the transmittance of the wavelength made incident on the interference filter lowers and wavelength shift occurs.

As described above, in the spectral instrument of this embodiment, a plurality of interference filters 31 through 39 that are made of dielectric multilayers and have different transmitting wavebands are disposed in order so that light reflected by a specific interference filter (for example, the interference filter 31) is made incident on the interference filter on the next stage (for example, the interference filter 32), and photodiodes 41 through 49 are provided at positions where light transmitted through the respective interference filters is made incident thereon. In this embodiment, at least on the light incidence surface side of the interference filter 31 on the first stage, a silver thin film 31 with a thickness of 20 to 200 nm is provided.

In this spectral instrument, since the transmitting wavebands of the interference filters 31 through 39 are different from each other, light with different wavelengths is transmitted through the respective interference filters and detected by the photodiodes 41 through 49, whereby spectroscopy is carried out. The reflected light intensities of the interference filters 31 through 39 tend to attenuate rearward.

Therefore, to detect sufficient light in the rear-stage photodiodes (for example, the photodiode 49), in this spectral instrument, on the light incidence surface side of the interference filter 31 on the first stage from the light source 3, a silver thin film 31a with a thickness of 20 nm or more is provided to improve the reflection performance, and the thickness of the silver thin film 31a is set to 200 nm or less so as to prevent attenuation of the intensity of light to be transmitted through this interference filter. Thereby, a plurality of optic elements with different wavelengths can be detected with high detection efficiency.

Hereinafter, a detailed description is given.

Figure 2:
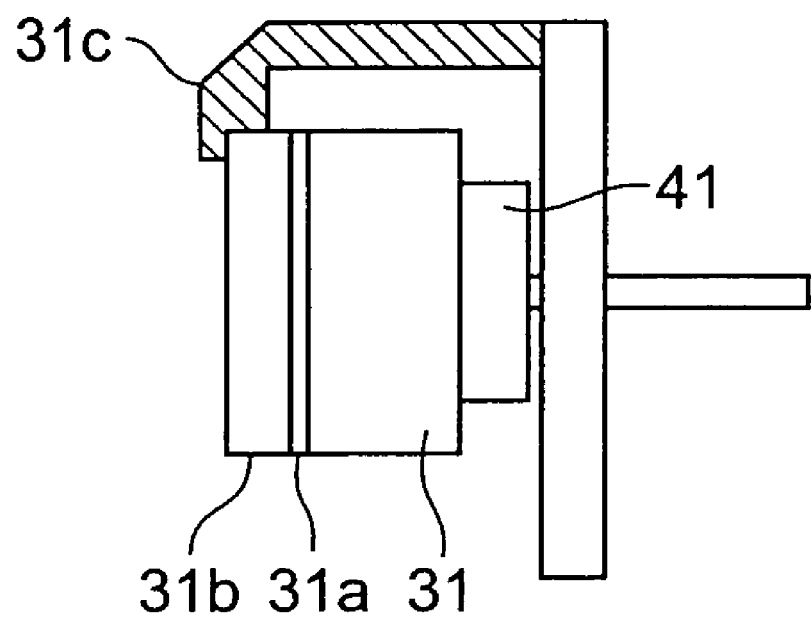
FIG. 2 is a partial enlarged view of a detector near a photodiode 31.

FIG. 2 is a partial enlarged view of a detector near the photodiode 31.

This spectral instrument has a light transmitting protection member 31b that sandwiches the silver thin film 31a with the interference filter 31. The silver thin film 31a is protected by the light transmitting protection member 31b. Light with a target wavelength (340 nm) transmitted through the light transmitting protection member 31b is transmitted through the silver thin film 31a and the interference filter 31 and reaches the photodiode 41. The photodiode 41 outputs an electrical signal in proportion to the intensity of the incident light. Wavelengths (incident light waveband—transmitting waveband) other than the target wavelength are reflected by the silver thin film 31a and the interference filter 31.

The light transmitting protection member 31b is made of glass. The glass is dampproof, so that by depositing silver thereon, silver oxidation can be prevented. Namely, the reflectance of silver deteriorates due to oxidation caused by air, so that by depositing the silver thin film 31a on the light transmitting protection member 31b, the reflection interface between the silver thin film 31a and the light transmitting protection member 31b is dampproofed.

After forming the silver thin film 31a, the silver thin film 31a is optically coupled with the interference filter 31. For this formation, a deposition method such as vapor deposition or sputtering, etc., is used. With the above-described construction, deterioration prevention and protection of the silver thin film 31a and optical coupling thereof to the interference filter 31 are realized. The target wavelength (340 nm) made incident on this detector is transmitted through the light transmitting protect member 31b, the silver thin film 31a, and the interference filter 31 in order with high efficiency, and wavelengths other than this are sufficiently reflected. The transmitting waveband of the light transmitting protection member 31b is set so as to include the transmitting wavebands of all the interference filters, and the light transmitting protection member is made of silica glass.

This spectral instrument is further provided with a pressing member 31c that presses the light transmitting protection member 31b against the interference filter 31 side so that the silver thin film 31a comes into close contact with the interference filter 31, and by this improvement in the degree of close contact, the optical coupling efficiency is improved. The pressing member 31c is provided to stand on the base portion of a holder, and engages with the light incidence surface and side surface of the light transmitting protection member 31b. The pressing member 31c may be made of an elastic resin or metal.

It is also allowed that a matching oil is filled between the silver thin film 31a and the interference filter 31. Or, the silver thin film 31a may be directly deposited on the interference filter 31. In this case, optical coupling between the interference filter and the silver thin film becomes easy. As a deposition method, vapor deposition or sputtering method can be used.

It is also possible that photomultipliers are used as photo-detecting devices instead of photodiodes.

Figure 3:
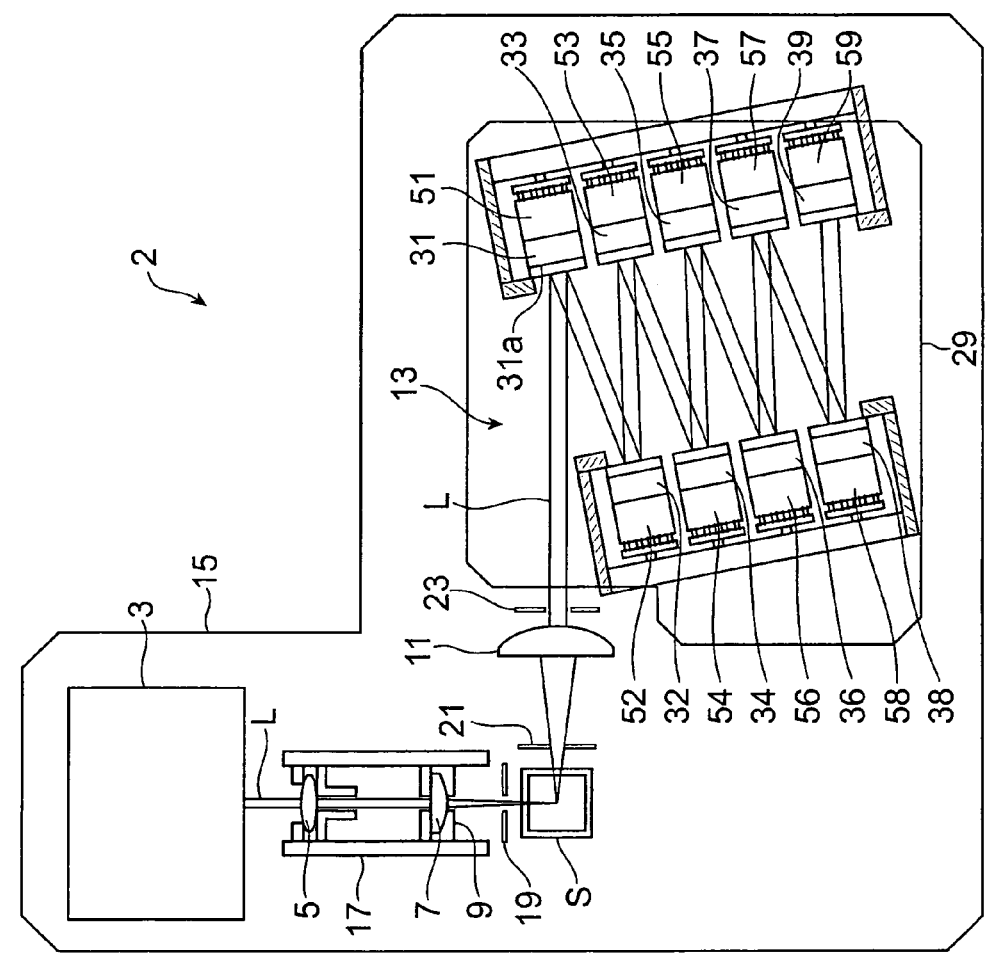
FIG. 3 is a constructional view of the spectral instrument 2 described above in which photomultipliers 51 through 59 are used as photodetecting devices 41 through 49.

FIG. 3 is a constructional view of the spectral instrument 2 constructed by using photomultipliers 51 through 59 as photodetecting devices 41 through 49 in the spectral instrument described above. In FIG. 3, the components equivalent to those of the spectral instrument shown in FIG. 1 are attached with the same symbols and description thereof is omitted.

In the spectral instrument 2, photomultipliers 51 through 59 as an example of the photodetecting devices are used instead of the photodiodes 41 through 49, and optic elements transmitted through the respective interference filters 31 through 39 are detected. When the intensity is extremely low like an optic element forming fluorescence, such an optic element that is hardly detected by the photodiodes 41 through 49 is detected by the photomultipliers 51 through 59.

In this example, the light path from the light source 3 is bent 90 degrees at the sample cell S. The reason for changing the advancing direction of the light L from the light source 3 by 90 degrees at the sample cell S is to prevent direct incidence of the light L from the light source 13 on the spectral part 13.

In other words, this spectral instrument has a lens 7 for making the light incident on the sample cell S from the light source 3, and the interference filter 31 on the first stage deviates from the extension of the optical axis of this lens 7. Thereby, detection reliability for each optic element is improved. The spectral instrument 2 shows the same effects as those of the spectral instrument 1.

According to the spectral instruments 1 and 2, optic elements of nine wavelengths are detected by providing nine interference filters that transmit optic elements with different wavelengths. However, the number of wavelengths to be detected by the spectral instrument is not limited thereto, and by changing the number of interference filters that transmit optic elements with different wavelengths, the number of wavelengths can be arbitrarily set.

In addition, in the spectral instruments 1 and 2, light that has been outputted from the sample cell S is roughly collimated by the lens 11 and then made incident on the interference filter, and when absorbance of the specific wavelength by the interference filter is great or when the intensity of the specific wavelength is small in light that exits from the light source or the sample, efficient spectroscopy is enabled by focusing on this filter. For example, in this embodiment, by focusing on the 340 nm interference filter 31, the detecting light amount can be improved, and the difference in light intensity to be detected by another interference filter can be reduced.

In this spectral instrument, the plurality of interference filters divide each incident light into optic elements to be reflected and an optic element to be transmitted, the optic elements to be reflected are made incident on the interference filter positioned next, and light from the light source is transmitted to the plurality of interference filters in order, whereby multi-wavelengths are detected. According to the inventor, it was found that the dielectric layer forming the interference filter had the property of reflecting comparatively well optic elements with wavelengths other than the optic element with a wavelength to be transmitted through the interference filter. Therefore, comparatively high-intensity light is made incident on the interference filter positioned in the rear of the order, so that multi-wavelengths can be detected with high detection efficiency.

In addition, according to this spectral instrument, incident light on each interference filter is divided into an optic element to be transmitted and optic elements to be reflected, and the optic elements to be reflected are made incident on the interference filter positioned next, so that multi-wavelengths can be detected at high speed. According to this spectral method, multi-wavelengths can be detected at high speed with high detection efficiency.

In addition, the spectral instrument according to the above-described embodiment has a plurality of photodetectors (the light transmitting protect member, the silver thin film, the interference filters, the photodetecting devices) that are arranged so that light is made incident thereon in time series at the speed of light, and each of the photodetectors has a photoelectric converter and an interference filter fixed to the light incidence side of the photoelectric converter, and the transmitting wavelength and the reflecting waveband are different among the interference filters, and the transmitting wavelength of the interference filter on the rear stage is included in the reflecting waveband of the interference filter on the previous stage. Herein, regardless of the transmitting wavelength of the interference filter, a full-reflecting mirror having an aperture can be provided on its light incidence surface side.

Figure 4:
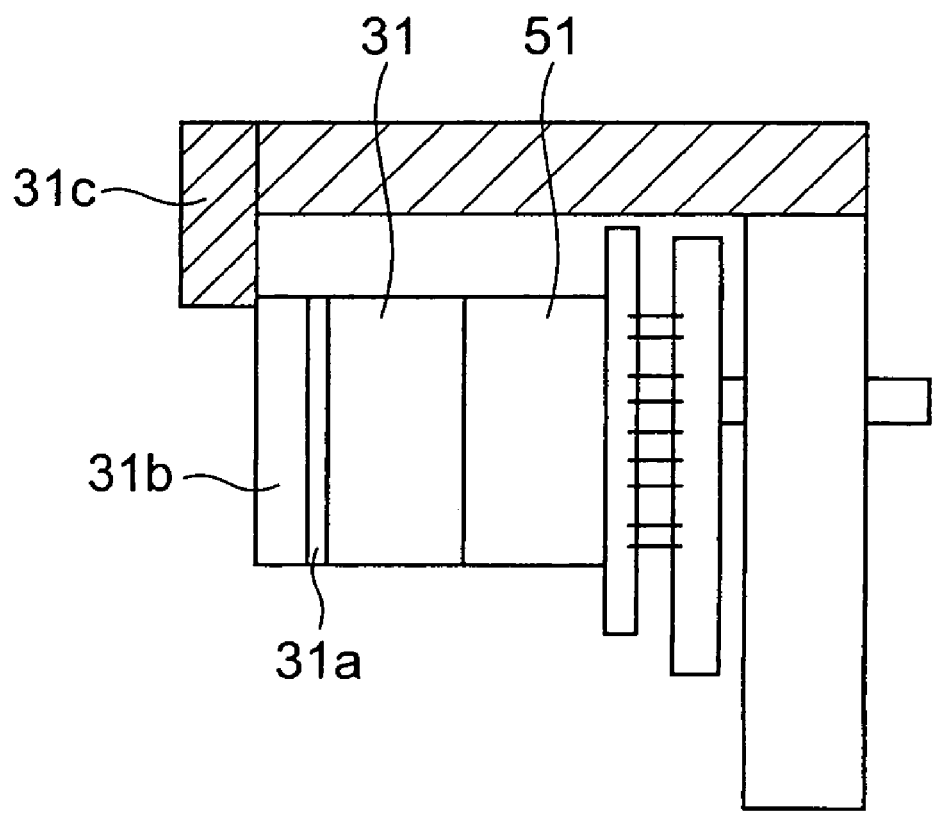
FIG. 4 is a partial enlarged view of a detector near the photomultiplier 51 on the first stage.

FIG. 4 is a partial enlarged view of the detector near the photomultiplier 51 on the first stage. The photomultiplier 51 is a head-on type photomultiplier that is formed by sealing the light incidence side opening of a metal side tube, forming a photoelectric surface on the inner surface of the glass surface plate, and providing a dynode group and an anode on the side tube interior.

In this spectral instrument, a light transmitting protection member 31b that sandwiches the silver thin film 31 with the interference filter 31 is also provided. The silver thin film 31a is protected by the light transmitting protection member 31b. Light with a target wavelength (340 nm) transmitted through the light transmitting protection member 31b is transmitted through the silver thin film 31a and the interference filter 31 and reaches the photomultiplier 51. The photomultiplier 51 outputs an electrical signal in proportion to the intensity of the incident light. Wavelengths (incident light waveband—transmitting waveband) other than the target wavelength are reflected by the silver thin film 31a and the interference filter 31.

In this spectral instrument, a pressing member 31c is also further provided to press the light transmitting protection member 31b against the interference filter 31 side so that the silver thin film 31a comes into close contact with the interference filter 31, and by this improvement in close contact, the optical coupling efficiency can be increased. The pressing member 31c is provided to stand from the base portion of a holder and engages with the light incidence surface and the side surface of the light transmitting protection member 31b. The pressing member 31c can be made of an elastic resin or metal, and it is also possible that a matching oil is filled between the silver, thin film 31a and the interference filter 31. Or, the silver thin film 31a may be directly deposited on the interference filter 31.

In the above-described photodetectors, the silver thin film and the light transmitting protect member are provided only in the first-stage photodetector, however, these can be provided in photodetectors on other stages in the same manner on the light incidence surface sides of the interference filters.

By disposing the plurality of photodetectors in a circular form, the air flow passage to the inside of the circular form becomes narrow, so that output fluctuations of the photodetectors caused by air fluctuation can be prevented.

In addition, by disposing an infrared ray cut filter in front of the photodetectors, occurrence of noises caused by infrared rays can be restrained, and by coloring the inner surface of the cylinder that forms the photodetector in black, noises caused by the cylinder inner surface reflection can be restrained.

The above-described interference filter is an optical filter that is formed by laminating a number of thin films with predetermined optical thicknesses formed by vapor-deposition or the like on a substrate and transmits or reflects only light of a specific waveband by using interference occurring inside. Generally, the interference filter is formed of a multi-layer dielectric film (for example, $SiO_2$, $SiN$, $TiO_2$). According to the inventor, the dielectric film forming the interference filter reflects optic elements with wavelengths other than an optic element of a wavelength to be transmitted by this interference filter at a comparatively high percentage (for example, 80% or more). Such an interference filter is sold by various manufacturers.

Figure 5:
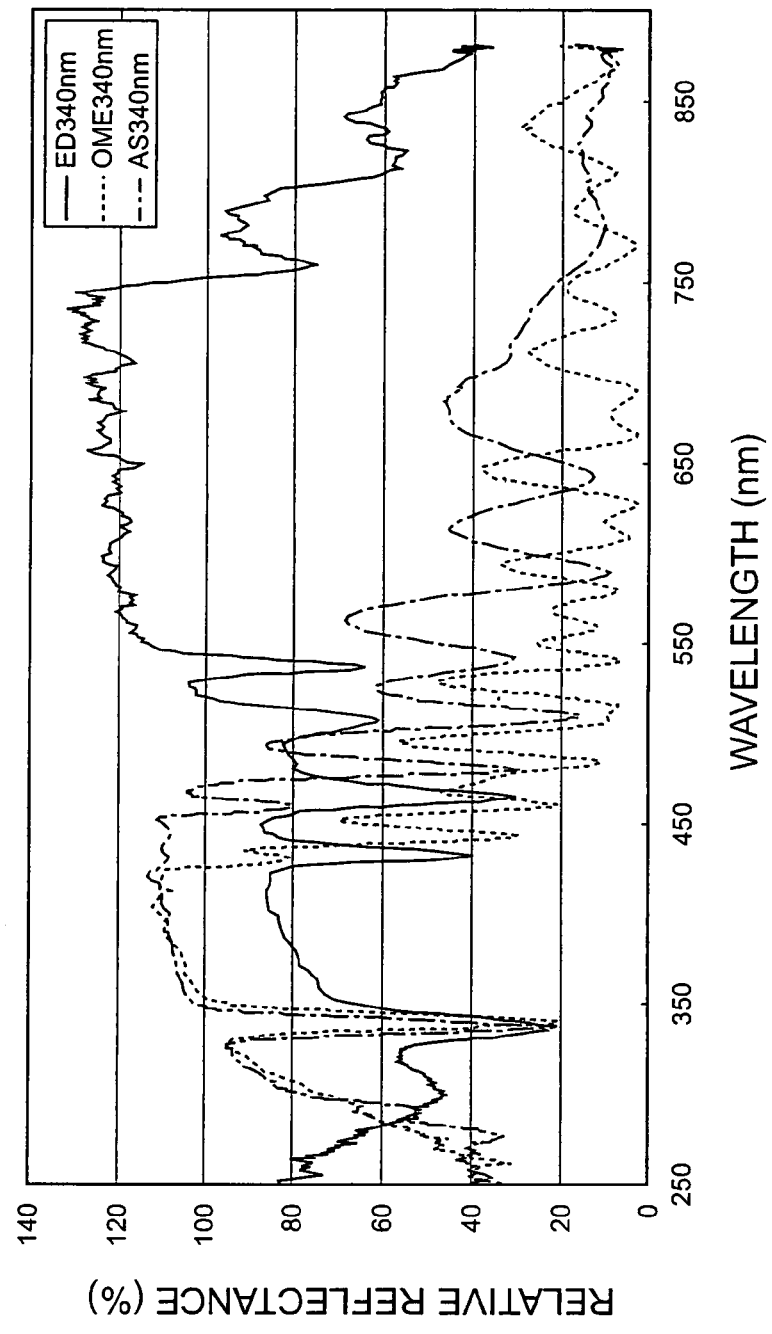
FIG. 5 is a graph showing a relative reflectance (%) with respect to a wavelength (nm) of an interference filter (340 nm) on the first stage when the silver thin film is not provided.

FIG. 5 is a graph showing a relative reflectance (%) with respect to the wavelength (nm) of the interference filter (340 nm) on the first stage when no silver thin film is provided. The angle of incidence θ on the interference filter is 8°. It is shown that all manufacturers' interference filters become low in reflectance for wavelengths other than a target wavelength, for example, 470 nm although they transmit the target wavelength (340 nm), and the photodetector on the rear stage cannot detect sufficient light intensity. ED 340 nm, OME 340 nm, and AS 340 nm are made by Edmund, Omega, and Asahi Spectra, respectively.

Figure 6:
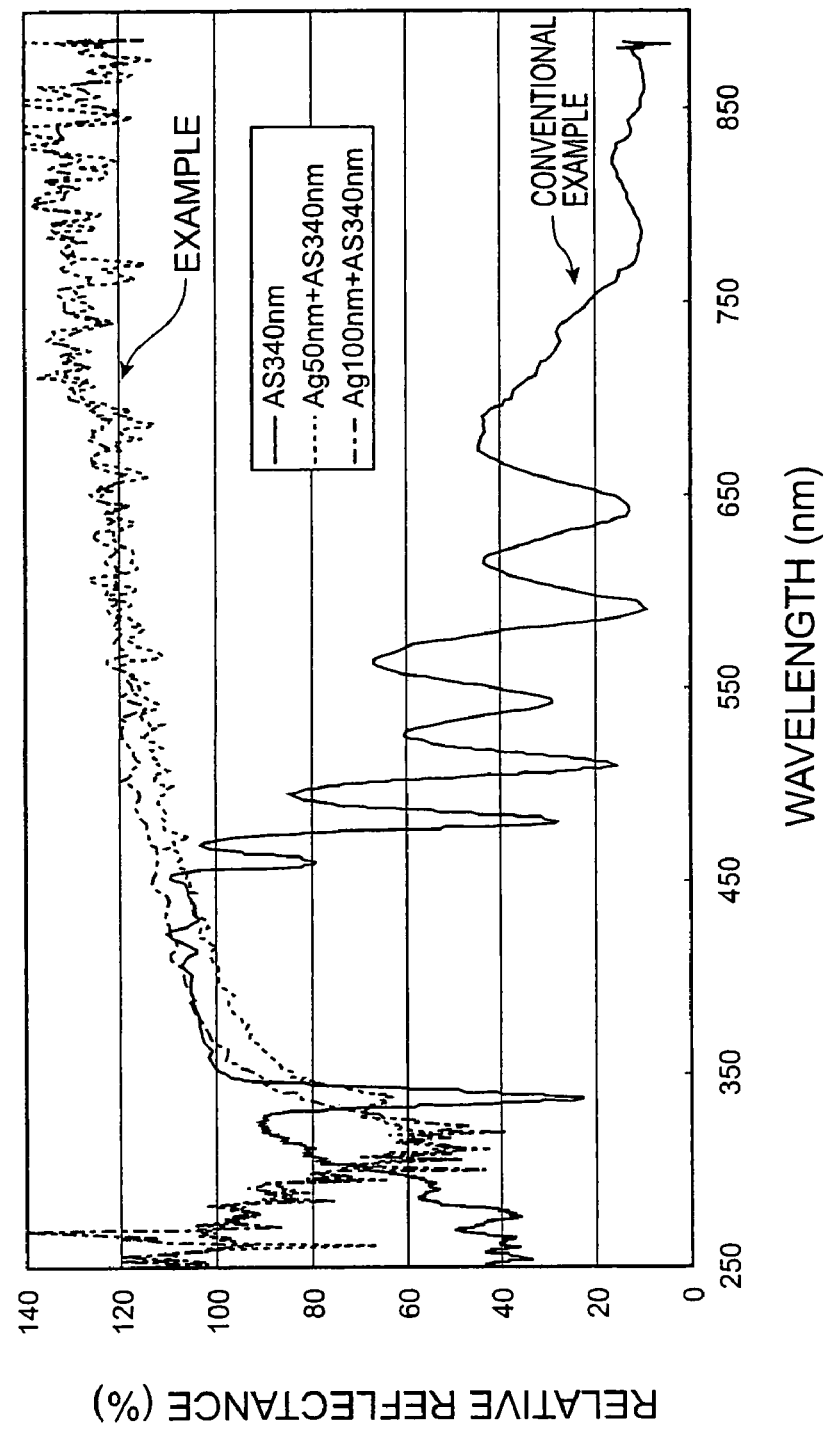
FIG. 6 is a graph showing a relative reflectance (%) with respect to a wavelength (nm) of an interference filter (340 nm) on the first stage when the silver thin film is provided.

FIG. 6 is a graph showing a relative reflectance (%) with respect to the wavelength (nm) of the interference filter (340 nm) on the first stage when the silver thin film is provided. The angle of incidence θ on the interference filter is 8°. When no silver thin film is provided (conventional example: AS 340 nm), the reflectance for a wavelength of 470 nm or more is greatly lowered, however, when silver thin films with thicknesses of 50 nm and 100 nm are provided (Ag 50 nm+AS 340 nm, Ag 100 nm+AS 340 nm), the reflectance does not lower even at a wavelength of 450 nm or more. Therefore, in the spectral instrument according to the above-described embodiment, sufficient light intensity can be detected even by the photodetector on the rear stage.

The above-described spectral instrument 1 was manufactured by way of trial and characteristics thereof were evaluated. As an interference filter, AS 340 nm was used, no sample cell was used and output values were measured.

FIG. 7 is a table showing output values (nA) from photodiodes for each channel (Ch) in the spectral instrument. The output values are in proportion to the transmitting light amounts of the interference filters. In this table, the case where no silver thin film is provided for the interference filters is raised as a conventional example using only band-pass filters, and the case where the thickness of the silver thin film is changed between 20 nm and 100 nm is raised as an example.

Figure 8:
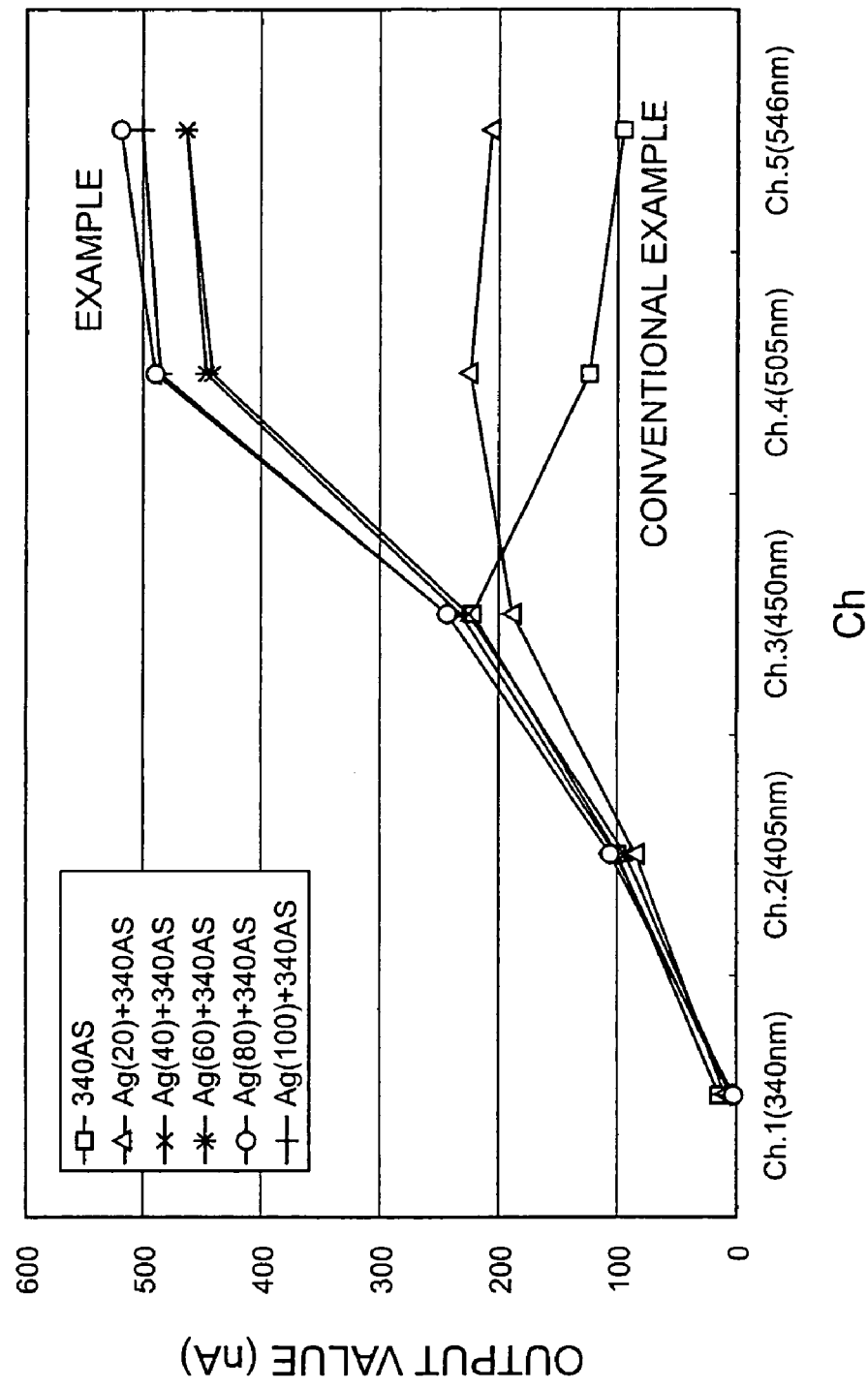
FIG. 8 is a graph showing the results of the table of FIG. 7.

FIG. 8 is a graph showing the results of the table of FIG. 7. As the interference filter, the above-described AS 340 nm (shown as 340 AS) is used, and the numerals in the parentheses indicate the thicknesses (nm) of the silver thin films. As shown in this graph, in the conventional example, the output value (nA) lowers in the regions (ch4 and ch5) of 450 nm or more wavelengths, and on the other hand, in the spectral instrument according to the example, the output value (nA) increases when the silver thin film thickness is 20 nm or more. Even when the silver thin film thickness is 100 nm, a lowering of the output value (nA) is not shown, however, when the thickness exceeds 200 nm, the output of the photodetector (ch1) on the first stage significantly lowers.

Figure 11:
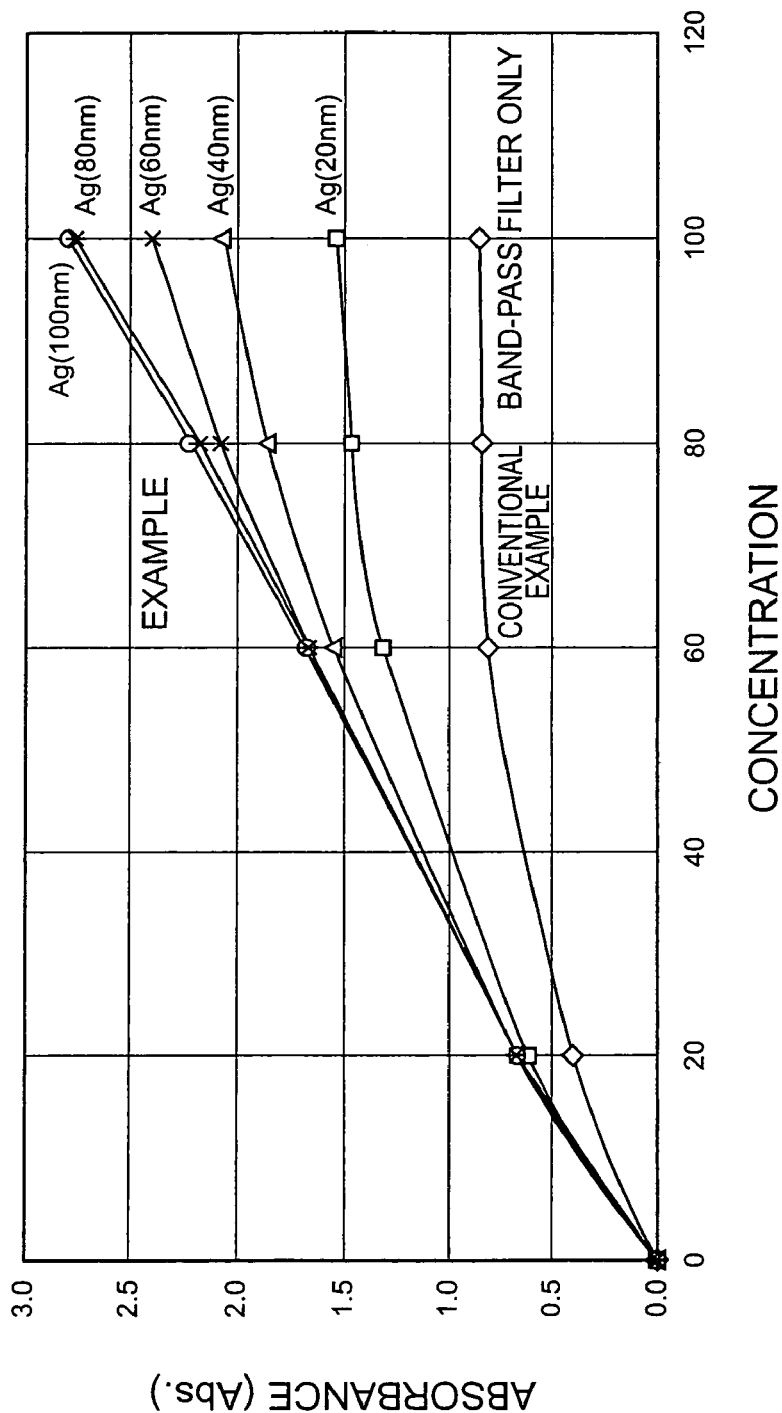
FIG. 11 is a graph showing the results of the table of FIG. 10.

FIG. 9 is a table showing output values (nA) of the photodetector on the first stage when β-NADH (substance for absorbing the transmitting wavelength (340 nm) of ch1) is put in the sample cell, FIG. 10 is a table in that the output values shown in FIG. 9 are converted into absorbances, and FIG. 11 is a graph showing the results of the table of FIG. 10. The concentration of β-NADH was changed from 0 to 100%, and changes in absorbance (Abs) were monitored.

The absorbance increases in proportion to the increase in β-NADH concentration, however, in the case of the conventional example, the absorbance tends to be saturated when the concentration becomes 60% or more, and it is understood that accurate absorbance measurement was not carried out. On the other hand, when the thickness of the silver thin film is 20 nm, the linearity of absorbance with respect to the concentration increases, and the linearity further increases at the thickness of 60 to 100 nm.

As described above, the above-described spectral instrument can detect a plurality of optic elements with different wavelengths with high detection efficiency, and can be used for examination of many samples and many items such as a blood test.

According to the spectral instrument of the invention, a plurality of optic elements with different wavelengths can be detected with high detection efficiency.

INDUSTRIAL APPLICABILITY

The invention can be used for a spectral instrument to be used for, for example, a blood test.

The invention claimed is:

1. A spectral instrument, including a plurality of interference filters that are made of dielectric multilayer films and have transmitting wavebands different from each other, and arranged in order so that light that has been reflected by a specific interference filter is made incident on an interference filter on the next stage, and photodetecting devices provided at positions on which the light that has been transmitted through the respective interference filters are made incident, including a silver thin film with a thickness of 20 to 200 nm is provided on the light incidence surface side of the interference filter on the first stage.

2. The spectral instrument according to claim 1, wherein a light transmitting protection member that sandwiches the silver thin film with the interference filter is provided.

3. The spectral instrument according to claim 2, wherein the light transmitting protection member is made of glass, and after depositing the silver thin film on the light transmitting protection member, the silver thin film is optically coupled with the interference filter.

4. The spectral instrument according to claim 3, further including a pressing member that presses the light transmitting protection member against the interference filter side so that the silver thin film comes into close contact with the interference filter.

5. The spectral instrument according to claim 1, wherein the silver thin film is directly deposited on the interference filter.

6. The spectral instrument according to claim 1, wherein a sample cell is disposed within a light path between a light source and the interference filter on the first stage.

7. The spectral instrument according to claim 6, including a casing that houses the light source, the sample cell, the interference filters, and the photodetecting devices.

8. The spectral instrument according to claim 1, wherein the thickness of the silver thin film is 60 to 100 nm.

9. The spectral instrument according to claim 1, wherein the angle of incidence θ of light on the interference filter on the first stage is greater than 0° and equal to or smaller than 10°.

10. The spectral instrument according to claim 9, wherein the angle of incidence θ of light on the interference filter on the second stage is greater than 0° and equal to or smaller than 10°.

11. The spectral instrument according to claim 6, including a lens that makes light incident on the sample cell from the light source, wherein the interference filter on the first stage deviates from the extension of the optical axis of this lens.

* * * * *